United States Patent
Yang et al.

(10) Patent No.: US 6,386,676 B1
(45) Date of Patent: May 14, 2002

(54) REFLECTIVE TYPE MEDIA SENSING METHODOLOGY

(75) Inventors: Changguo Mike Yang; Chen Liu; Seng San Koh, all of Singapore (SG)

(73) Assignee: Hewlett-Packard Company, Palo Alto, CA (US)

( * ) Notice: Subject to any disclaimer, the term of this patent is extended or adjusted under 35 U.S.C. 154(b) by 0 days.

(21) Appl. No.: 09/757,068

(22) Filed: Jan. 8, 2001

(51) Int. Cl.$^7$ ............................................. G01N 21/86
(52) U.S. Cl. ............... 347/19; 250/559.01; 250/559.49; 399/389; 400/708
(58) Field of Search ............................... 347/19, 14, 16, 347/104; 250/559.01, 559.06, 559.07, 559.16, 559.27, 559.49, 559.4; 400/708; 356/446; 399/389; 271/258.01, 265.01

(56) References Cited

U.S. PATENT DOCUMENTS

| | | | |
|---|---|---|---|
| 3,902,713 A | * 9/1975 | Von Luhmann | 271/154 |
| 4,540,887 A | * 9/1985 | Minerd et al. | 250/559.4 |
| 4,881,086 A | * 11/1989 | Misawa | 347/248 |
| 4,937,460 A | * 6/1990 | Duncan et al. | 250/559.27 |
| 4,994,678 A | * 2/1991 | Sasaki | 250/559.4 |
| 5,109,236 A | * 4/1992 | Watanabe et al. | 347/193 |
| 5,139,339 A | * 8/1992 | Courtney et al. | 356/446 |
| 5,751,443 A | * 5/1998 | Borton et al. | 356/446 |
| 5,754,213 A | * 5/1998 | Whritenor | 347/218 |
| 5,764,251 A | * 6/1998 | Hashimoto | 347/16 |
| 5,903,380 A | * 5/1999 | Motamedi et al. | 359/224 |
| 6,217,168 B1 | * 4/2001 | Elgee | 347/105 |

* cited by examiner

*Primary Examiner*—John Barlow
*Assistant Examiner*—Blaise Mouttet (57) ABSTRACT

A printer, which can detect a media sheet type, includes: a light emitting source and a reflector, the light emitting source being capable of emitting light in a light emission direction towards the reflector, the reflector being arranged in light emission direction and being capable of reflecting light emitted by the light emitting source in a light reflection direction; a detector being arranged such that it can detect reflected light; and a controller connected to the reflector, the controller being capable of modulating a characteristic of the reflected light.

11 Claims, 6 Drawing Sheets

REFLECTIVE TYPE MEDIA SENSING METHODOLOGY

BACKGROUND OF THE INVENTION

The invention discloses a printer, which can detect a media sheet, and a method of detecting a media sheet in a printer, wherein especially the type of the media sheet can be detected.

The invention relates especially to media sheets used for instance in printers which are based on the inkjet principle. An inkjet printer fires little droplets of ink onto the used media sheet, where the droplets are absorbed. After drying of the ink of one droplet a more or less little printed dot remains on the media sheet according to the absorbency of the media sheet. Every media sheet accepts a maximum amount of ink due to its characteristic maximum absorption of humidity. If an inkjet printer is operated such that it fires more droplets than the media sheet can absorb, i.e., the adjusted amount of ink at the printer is higher than the maximum amount of ink of the media sheet, the surplus ink is not absorbed any more from the media sheet. The surplus ink, which is too much for absorption, causes two main problems. The first problem is, that the surplus ink is smeared over the media sheet onto areas, where corresponding ink is not desired. The second problem is, that the surplus ink remains in contact with the nozzle of the print head of the inkjet printer and dries on the nozzle. This causes a blockage of the nozzle of the inkjet printer. Due to this blockage many cleaning runs or even an exchange of the inkjet print head become necessary.

Media sheets as used for instance in printers like inkjet printers are mainly known as normal paper sheets, as photo paper sheets or as transparencies. These media sheets have a different maximum absorption of humidity due to their consistence. Hence, dependent on the used media sheet the printer should only print with the maximum amount of ink corresponding to the used media sheet to avoid a surplus of ink and, therefore, to avoid the above mentioned problems caused by surplus ink.

To protect the printer by and to relieve the user on adjusting the correct amount of ink in a printer driver, printers according to the prior art make use of a C-shaped photo-interrupter or a reflective sensor. However, both the C-shaped photo-interrupter and the reflective sensor have some disadvantages, which will be now described together with their function.

The C-shaped photo-interrupter comprises a light emitter and a light receiver, which are arranged opposite to one another on the ends of a C-shaped holding element with a gap in between. The light receiver receives in an undisturbed mode direct light emitted by the light emitter. If a non-transparency media goes through the gap between the light emitter and the light receiver and blocks the direct light, the light receiver is in a disturbed mode and does not receive any direct light any more. This blockage will cause a receiver output current change, which indicates, that a non-transparency sheet is placed in the gap in between the C-shaped photo-interrupter. This detector has the disadvantages, that the media sheet has to be guided through the gap of the detector or the gap of the detector has to be placed very exactly at the media path through the printer, respectively, and that the detector only detects the difference between transparencies and non-transparencies.

The reflective sensor comprises a light emitter and a sensor for detecting light, which was emitted by the light emitter and reflected by a media sheet. The reflective sensor detects the level of the reflected light to determine the media sheet type, as different media have different reflective characteristics. However, this detector has the disadvantages, that it largely depends on the distance as well as the angle between the media sheet and the detector, and that it is very difficult to characterize the reflective level of a transparency, as a transparency has both reflective and transparent characteristics. A slight change in the distance between the detector and the media sheet or a slight change of the angle of the media sheet with respect to the detector will cause very big output level changes.

SUMMARY OF THE INVENTION

An object of the invention is to detect a media sheet used in a printer with regard to its type and existence, wherein the way of detection is universally applicable, i.e., it should not require any changes of the media sheet path through the printer and should detect and identify media sheets reliably.

The object is achieved by a printer, which can detect media sheets, and a method of detecting a media sheet according to the independent claims.

A printer, which can detect a media sheet type, comprises: a light emitting source and a reflector, the light emitting source being capable of emitting light in a light emission direction towards the reflector, the reflector being arranged in light emission direction and being capable of reflecting light emitted by the light emitting source in a light reflection direction; a detector being arranged such that it can detect reflected light; and a controller connected to the reflector, the controller being capable of modulating a characteristic of the reflected light.

A method of detecting a media sheet in a printer according to the invention comprises the following steps: emitting light by a light emitting source towards a reflector; reflecting light emitted by the light emitting source by the reflector and/or a media sheet, which has a given type and which can be arranged between the light emitting source and the reflector, in a light reflection direction; generating a signal corresponding to reflected light by a detector; modulating a characteristic of the reflected light by a controller connected to the reflector; and using the signal generated by the detector for detecting the media sheet.

One advantage of the invention over the prior art is that not only transparencies and non-transparencies but also normal paper and photo paper can be identified. Another advantage of the invention is that the media sheets must not be guided outside a normal printing path of a printer, which is provided according to the invention. A further advantage of the invention is that the printer can be self-calibrated to ensure reliable measurement. Such a self-calibration possibility requires no user intervention and saves manufacturing process time and, therefore, reduces manufacturing costs.

The above and other objects, features and advantages of the present invention will become apparent from the following description and the appended claims, taken in conjunction with the accompanying drawings in which like parts or elements are denoted by like reference numbers.

DETAILED DESCRIPTION OF PREFERRED EMBODIMENTS OF THE INVENTION

Preferred embodiments of the invention will now be described with reference to the attached drawings in which like parts or elements are denoted by like reference numbers.

Figure 1:
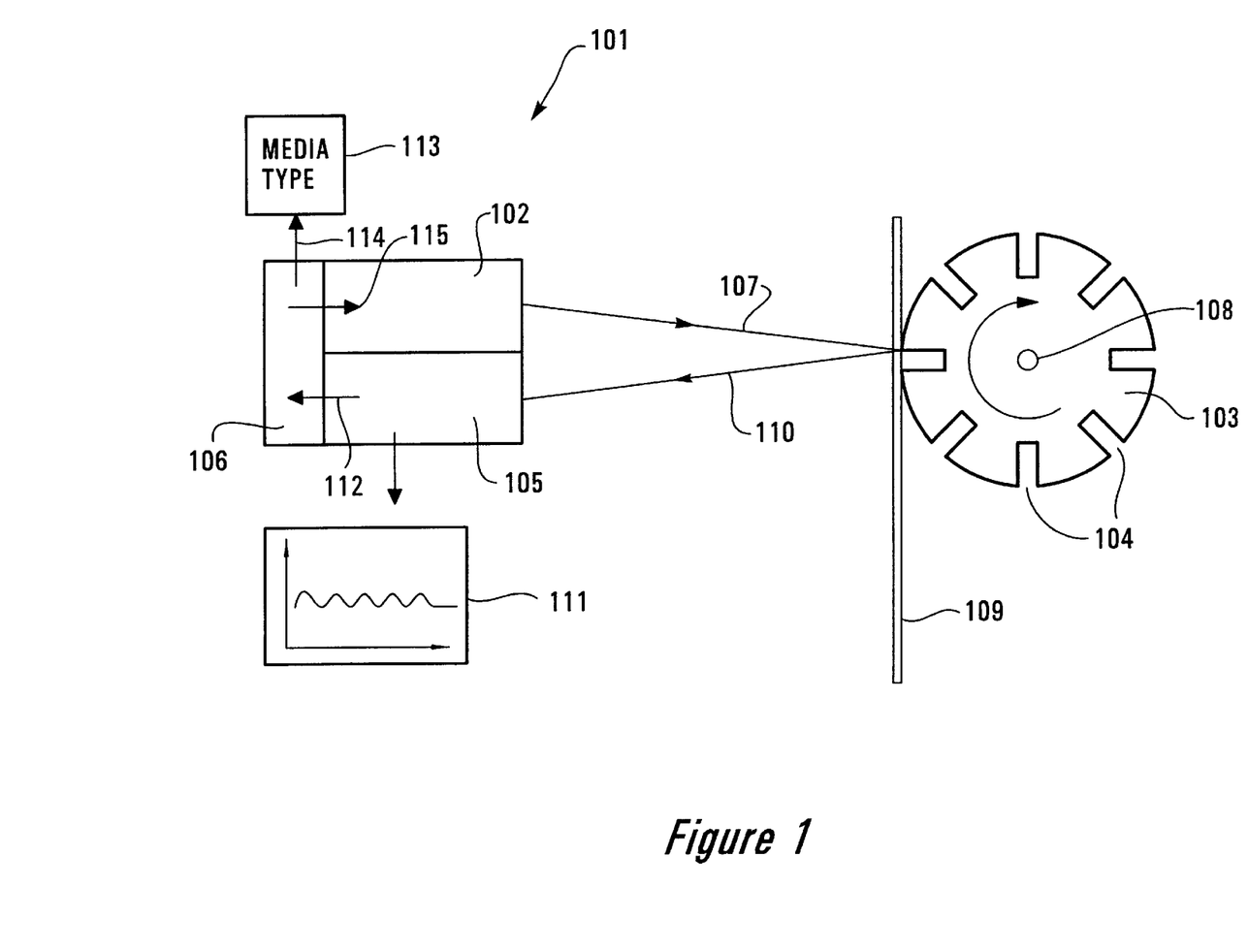
FIG. 1 shows a schematic side view of a first embodiment of the invention.

FIG. 1 shows a schematic side view of a detector unit 101 of a printer according to a first embodiment of the invention. The detector unit 101 comprises a light emitting source 102, a roller disk 103 with slots 104 as reflector, a detector 105 and an analyzing element 106.

The reflector is designed for having patterns with different reflective characteristics such as different light reflection directions and/or different amounts of reflected light. In the embodiments according to the invention this reflector is carried out for instance by the roller disk 103 with slots 104. The light emitted by the light emitting source 102 towards the roller disk 103 is reflected by an outside surface of the rotating roller disk 103 or by the slots 104 in the roller disk 103 as long as no media sheet is present. Therefore, the slots 104 represent the pattern of the reflector having different reflective characteristics. This is due to the fact, that the outside surface of the roller disk 103 reflects more light than the slots 104 in the roller disk 103, because the slots 104 in the roller disk 103 have a greater distance to the detector 105 than the outside surface of the roller disk 103. It should be mentioned, that other designs of a reflector having patterns with different reflective characteristics can also be used.

The analyzing element 106 is connected to the light emitting source 102 and the detector 105. The light emitting source 102 emits light in a light emission direction 107 towards the roller disk 103. The roller disk 103 itself is connected to a controller 108 and arranged rotatable around an axis of rotation, which is perpendicular to the light emission direction 107 and falls in the controller 108. FIG. 1 shows the case that a media sheet 109 is positioned between the roller disk 103 and the light emitting source 102 as well as the detector 105. The detector 105 detects light, which is reflected from the roller disk 103 or the media sheet 109 in light reflection direction 110, and generates a signal 111 according to detected reflected light. The analyzing element 106 receives the signal 111 via a receiving connection 112, analyzes the signal 111 and emits a media type information 113 via a data connection 114 or controls the light emitting source 102 via a controlling connection 115. The controller 108 causes the roller disk 103 to rotate and, therefore, varies the light reflection direction 110 due to the slots 104.

As long as no media sheet 109 is moved between the roller disk 103 and the light emitting source 102 as well as the detector 105, the analyzing element 106 can execute self-calibration runs. Then, light is emitted in light emission direction 107 from the light emitting source 102 and reflected from the rotating roller disk 103 in light reflection direction 110. The detector 1 05 detects the reflected light in light reflection direction 110 and generates a corresponding signal 111. The analyzing element 106 receives the signal 111 via the receiving connection 112, analyzes the signal 111 and controls the light emitting source 102 via the controlling connection 115. If the signal 111 lies completely or partly outside of a predetermined value range, the analyzing element 106 adjusts the light emitting source 102 until the signal 111 lies constantly within the predetermined value range. The predetermined value range, which is necessary for these self-calibration runs, is stored in the analyzing element 106 for this purpose.

As already mentioned above, the analyzing element 106, which receives the signal 111 via the receiving connection 112, analyzes the signal 111 and emits a media type information 113 via a data connection 114. The analysis of the signal 111 is now described: First, the analyzing element 106 detects the shape of the signal 111. If the signal 111 has a nearly constant value, the analyzing element 106 checks, if the nearly constant value is greater than a predetermined threshold value. If this is true, the analyzing element 106 emits a first media type information 113. If the signal 111 has a nearly constant value lower than the predetermined threshold value, the analyzing element 106 emits a second media type information 113. If the signal 111 varies periodically between a maximum value and a minimum value, which are each higher than the predetermined maximum value or the predetermined minimum value, respectively, the analyzing element 106 emits a third media type information 113.

The controller 108 can be part of a line feed mechanism inside of a printer. Then, the controller 108 is preferably arranged such that a guided media sheet 109 reaches first the controller 108 and the detector unit 101 before it reaches the area, where printing takes place. Usually line feed mechanisms guide the media sheet through printers having each at least two normal roller disks at one guiding arbor. According to the invention it is preferred to add the roller disk 103 to the normal roller disks and to arrange the light emitting source 102 and the detector 105 as a combined sensor element such that the guided media sheet 109 moves between the roller disk 103 and the combined sensor element.

Figure 2:
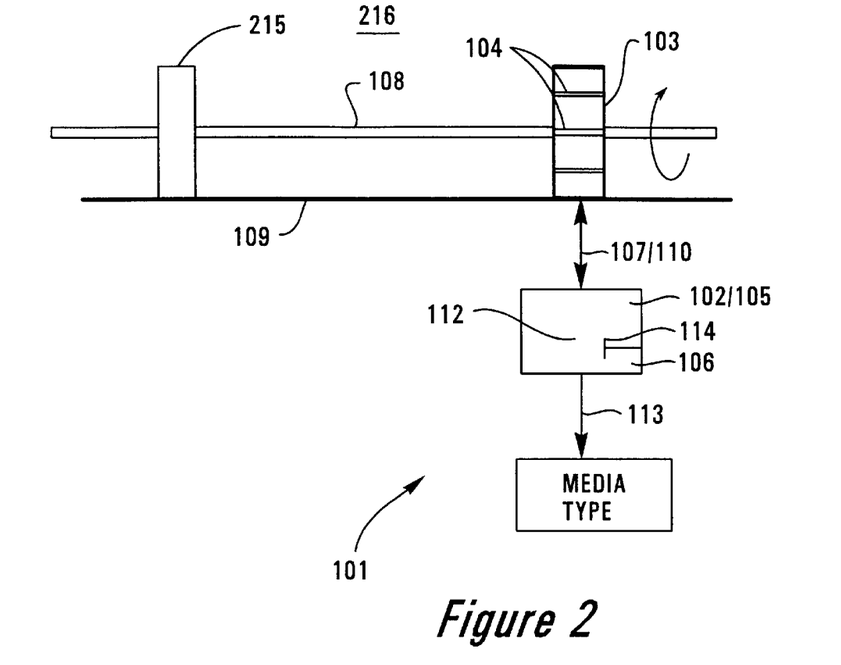
FIG. 2 shows a schematic top view of the first embodiment of the invention.

FIG. 2 shows a schematic top view of the detector unit 101 of the printer according to the first embodiment of the invention. The detector unit 101 comprises mainly the same elements as in FIG. 1. Additionally shown is a normal roller disk 216, which is connected to the controller 108 and arranged rotatable around the axis of rotation, which is perpendicular to the light emission direction 107 and falls in the controller 108. As mentioned in the description of FIG. 1 the controller 108 can be part of a line feed mechanism inside of a printer. Then, the controller 108 together with the roller disk 103 and the normal roller disk 216 represent a part of one guiding arbor of the line feed mechanism, which guides the media sheet along a media path through the printer.

Figure 3:
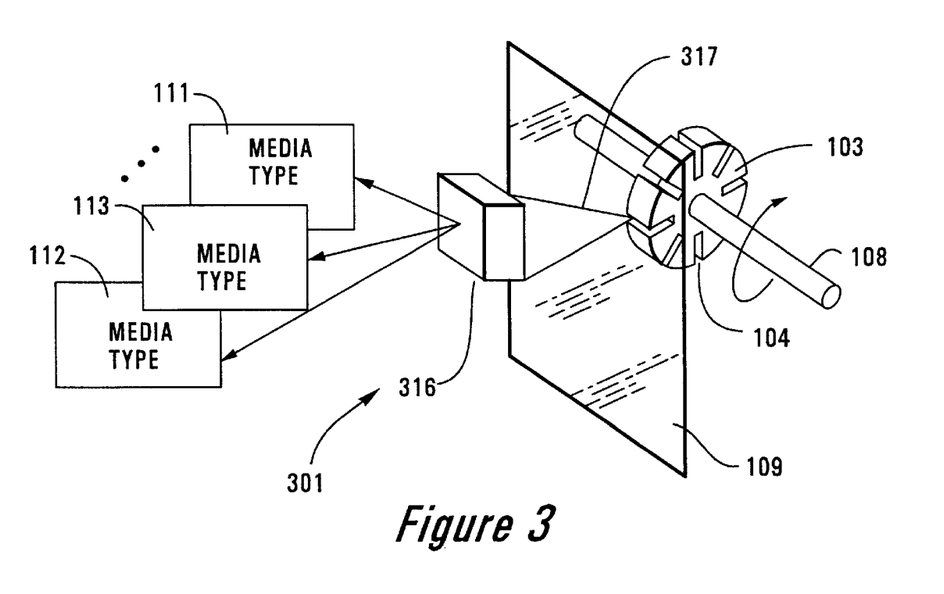
FIG. 3 shows a schematic three-dimensional view of a second embodiment of the invention.

In FIG. 3 a schematic three-dimensional view of a detector unit 301 of a printer according to a second embodiment of the invention is shown. The detector unit 301 comprises a combined sensor element 317, a roller disk 103 with slots 104 as reflector and a controller 108. The combined sensor element 317 comprises a light emitting source and a detector, who work in the same way as the already described corresponding components of the detector unit 101 of the printer according to the first embodiment of the invention. A media sheet 109 is placed between the roller disk 103 and the combined sensor element 317 as long as the media sheet 109 is moved along a media path in the printer. The combined sensor element 317 emits light towards the roller disk 103 and detects reflected light, which is reflected by the roller disk 103 and/or by a media sheet 109, and generates a signal 111 according to detected reflected light. The emitted light and the reflected light are combined and schematically shown as a light cone 318. Further, the signal 111 can be analyzed and a media type information 113 based on the signal 111 can be generated. Finally, self-calibration runs can be performed with the combined sensor element 317 in the same way as already described above for the individual components of the detector unit 101 of the printer according to the first embodiment of the invention.

Figure 4:
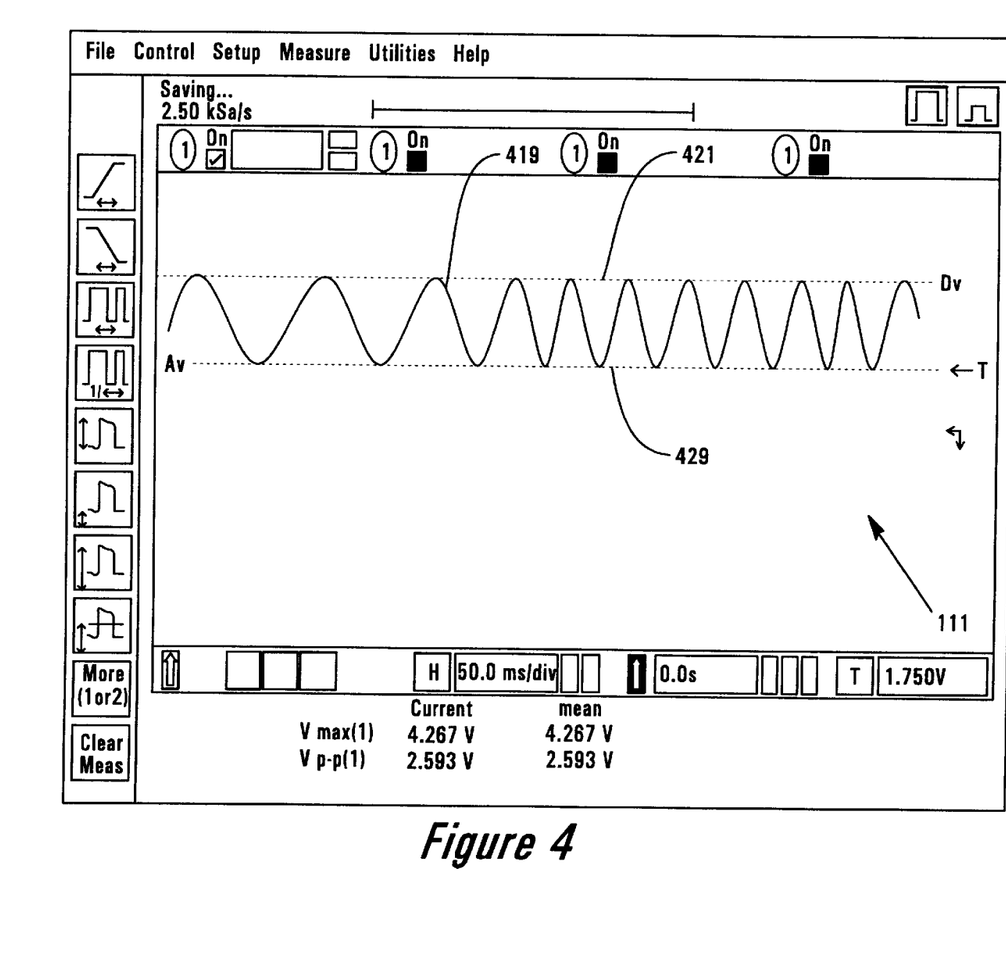
FIG. 4 shows a diagram of a signal as caused without any media sheet.

FIG. 4 shows a diagram of the signal 111 as caused without any media sheet. As long as no media sheet is fed in the media path of the printer between the detector unit 101 or 301, respectively, the roller disk 103 rotates around the controller 108 and the detector 105 detects the reflected light as well as generates the signal 111 according to the detected reflected light. The light emitted by the light emitting source 102 towards the roller disk 103 is reflected towards the detector 105 by an outside surface of the rotating roller disk 103 or by the slots 104 in the roller disk 103. The outside surface of the roller disk 103 reflects more light than the slots 104 in the roller disk 103, because the slots 104 in the roller disk 103 have a greater distance to the detector 105 than the outside surface of the roller disk 103. Therefore, the detected signal 111 looks like a sine wave 419 with a minimum value 420 and a maximum value 421 due to the rotation of the roller disk 103.

During a self-calibration run of the detector unit 101 or 301, respectively, such a signal 111 can also be detected. Then, if the minimum value 420 or the maximum value 421 lie outside of a stored value range, the analyzing element 106 adjusts the light emitting source 102 until the minimum value 420 and the maximum value 421 lie within the stored value range. Such a self-calibration run is necessary to enable reliable measurements during operation of the detector unit 101 or 301, respectively.

Figure 5:
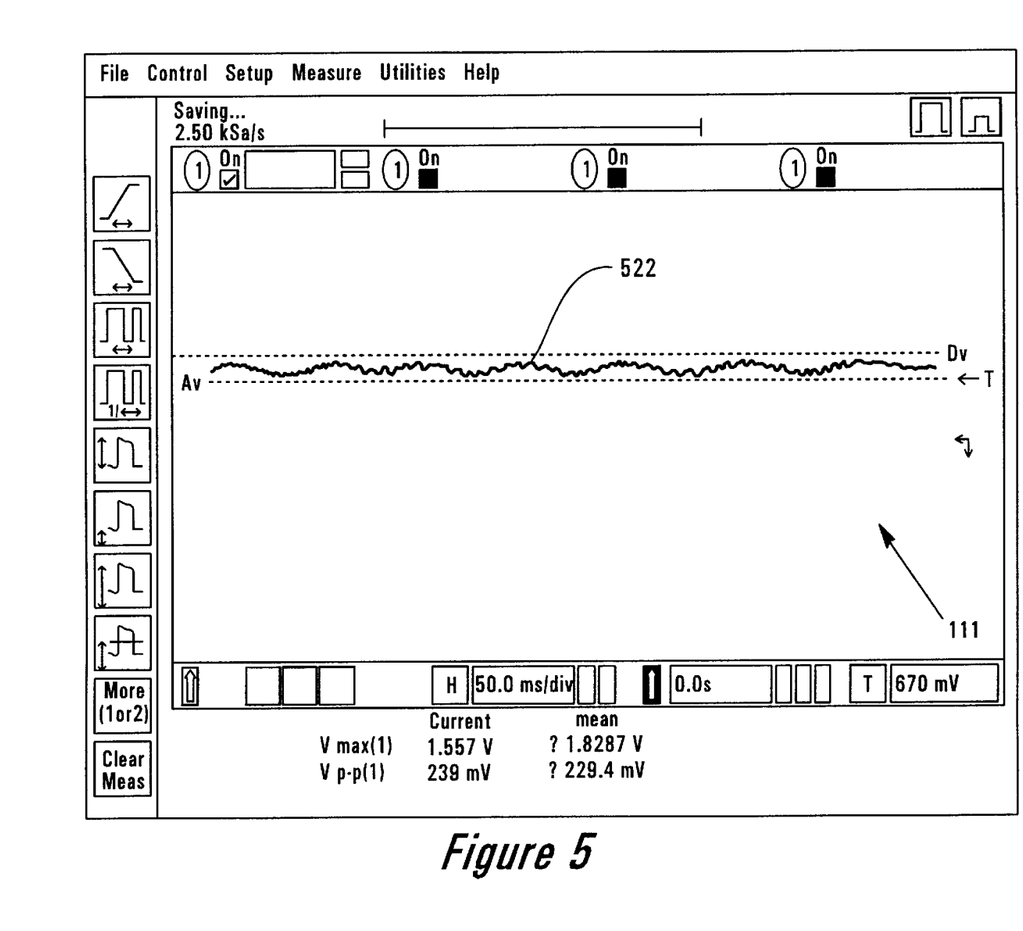
FIG. 5 shows a diagram of a signal as caused by a normal paper media.

In FIG. 5 a diagram of the signal 111 as caused by a normal paper media is shown. During movement of a non-transparent media sheet 109 in between the roller disk 103 and the light emitting source 102 as well as the detector 105, the roller disk 103 is blocked and the light emitted by the light emitting source 102 is reflected by the media sheet 109 towards the detector 105. Then, the detector 105 generates a signal 111 with a first nearly constant value 522 according to the detected reflected light. The fluctuations in the signal 111 can be caused by impurities in the media sheet 109 as well as by the moving action of the media sheet 109. Due to the first nearly constant value 522 of the signal 111, the analyzing element 106 emits "normal paper sheet" as media type information 113.

Figure 6:
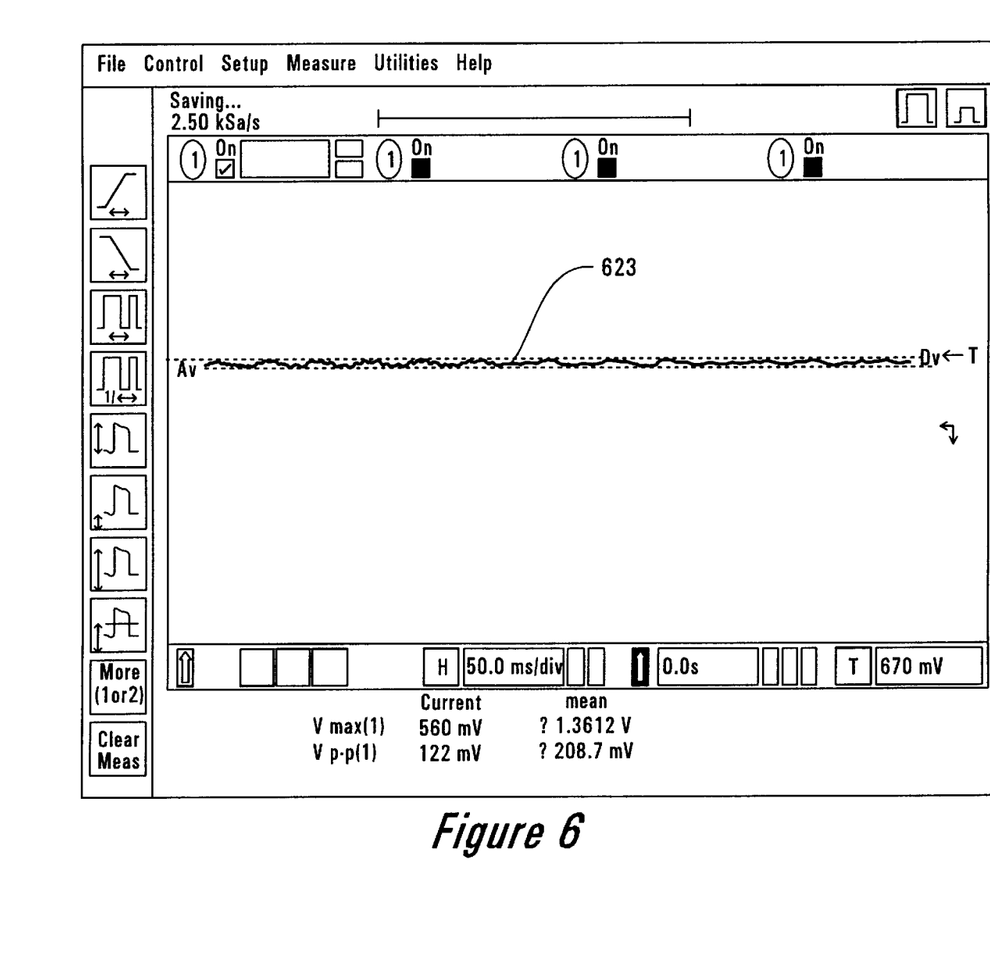
FIG. 6 shows a diagram of a signal as caused by a photo paper media.

FIG. 6 shows a diagram of the signal 111 as caused by a photo paper media. The generation of the signal 111 is similar to that described in FIG. 5. In contrast to FIG. 5, the signal 111 has a second nearly constant value 623, which is lower than the first nearly constant value 522. Due to the second nearly constant value 623 of the signal 111, the analyzing element 106 emits "photo paper sheet" as media type information 113.

Figure 7:
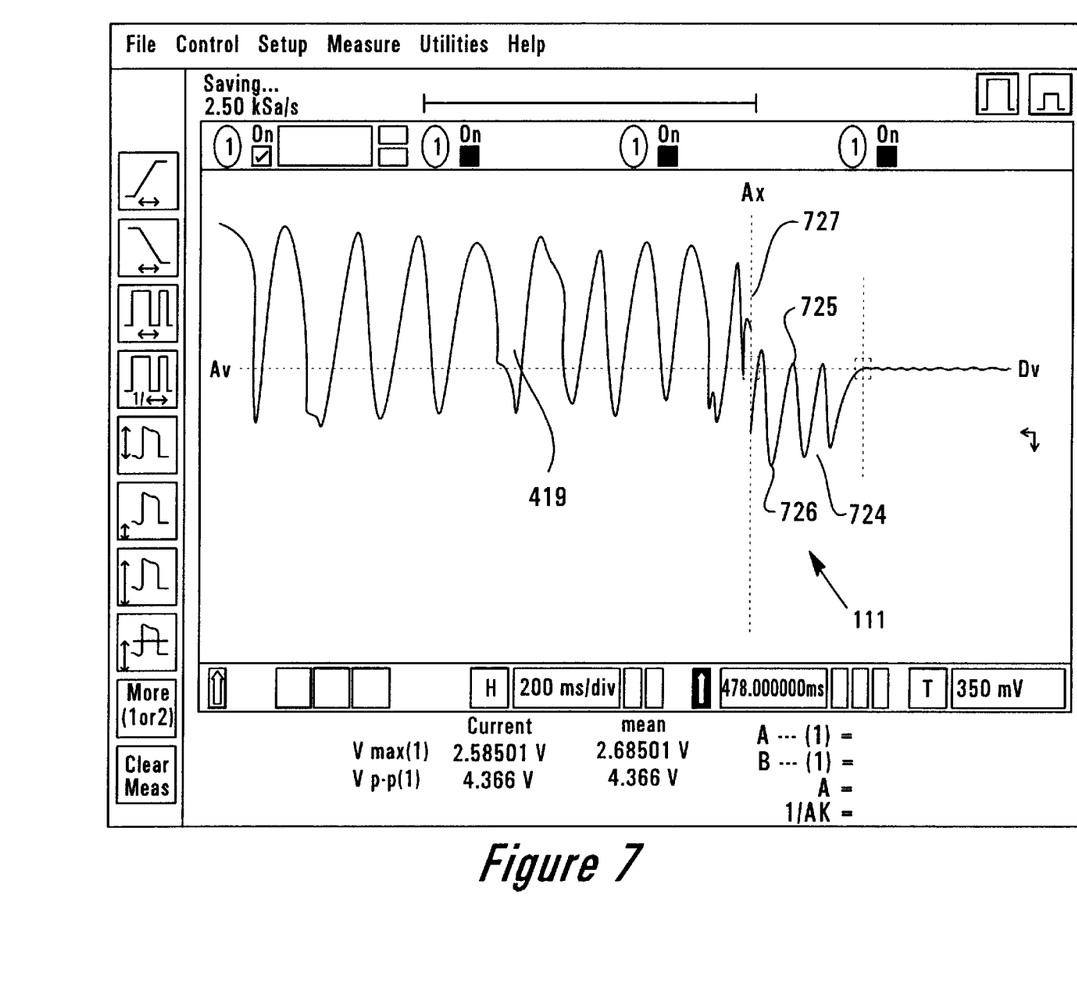
FIG. 7 shows a diagram of a signal as caused by a transparency.

Finally, FIG. 7 shows a diagram of the signal 111 as caused by a transparency. During movement of a transparent media sheet 109 in between the roller disk 103 and the light emitting source 102 as well as the detector 105, the light emitted by the light emitting source 102 is reflected towards the detector 105 partly by the media sheet 109, partly by an outside surface of the roller disk 103 and partly by the slots 104 in the roller disk 103. This is due to the fact, that a transparent media sheet 109 has both reflective and transparent components for incident light. The last two light reflection parts are caused by the rotating roller disk 103, because the roller disk 103 turns while the transparent media sheet 109 is moved through the detector unit 101 or 301, respectively. The detector 105 generates a signal 111 according to the detected reflected light, which looks like a periodic wave 724 with a minimum value 725 and a maximum value 726 due to different light components reflected by the transparent media sheet 109 as well as by the rotating roller disk 103. Due to both the minimum value 725 and the maximum value 726 of the signal 111, the analyzing element 106 emits "transparency" as media type information 113.

Additionally shown in FIG. 7 is a transition 727 of the signal 111 from a first mode to a second mode. In the first mode, no media sheet 109 is placed inside the detector unit 101 or 301, respectively. The signal 111 in the first mode is identical to the signal 111 as described in FIG. 4 and, therefore, looks like the sine wave 419 due to the rotation of the roller disk 103. In the second mode, the transparent media sheet 109 is placed inside the detector unit 101 or 301, respectively. The signal 111 in the second mode was already described above and looks like a periodic wave 724. Finally, the detection of the signal 111 under special consideration of the transition 727 yields an exact information in a printer about an arrival of a media sheet 109, on which printing should be performed.

What is claimed is:

1. A printer, comprising:
    a light emitting source and a reflector, the light emitting source being capable of emitting light in a light emission direction towards the reflector, the reflector being arranged in the light emission direction and being capable of reflecting light emitted by the light emitting source in a light reflection direction,
    a detector being arranged such that it can detect reflected light,
    a controller connected to the reflector, the controller being capable of modulating a characteristic of the reflected light, and
    a feeding mechanism which moves a media sheet through a position in which the reflector is located on one side of the media sheet and the light emitting source and the detector are both located on the other side of the media sheet.

2. The printer according to claim 1, wherein the media sheet either alone or in combination with the reflector is in a condition to reflect light emitted from the light emitting source to the detector for detecting type and presence of the media sheet.

3. The printer according to claim 1, wherein the characteristic of the reflected light is the light reflection direction.

4. The printer according to claim 3, wherein the controller varies the orientation of the reflector for changing the light reflection direction.

5. The printer according to claim 1, wherein the characteristic of the reflected light is the amount of the reflected light.

6. The printer according to claim 5, wherein the controller varies the position of the reflector for changing the amount of the reflected light.

7. The printer according to claim 1, wherein the controller varies reflecting characteristics of the reflector for changing the amount of the reflected light.

8. A method of detecting a media sheet in a printer, comprising the following steps:
    feeding a media sheet through a position in which a reflector is located on one side of the media sheet and a light emitting source and a detector are both located on the other side of the media sheet, emitting light by the light emitting source towards the reflector, reflecting light emitted by the light emitting source by the reflector and/or the media sheet, which has a given type and which is arranged between the light emitting source and the reflector, in a light reflection direction, generating a signal corresponding to the reflected light by the detector, modulating a characteristic of the reflected light by a controller connected to the reflector, and using the signal generated by the detector for detecting the media sheet.

9. The method according to claim 8, wherein the controller modulates the light reflection direction by varying the orientation of the reflector.

10. The method according to claim 8, wherein the controller modulates the amount of the reflected light by varying the position of the reflector.

11. The method according to claim 8, wherein the media sheet having a media sheet type is moved between the light emitting source and the reflector, and wherein the media sheet type changes the reflected light at the detector.

* * * * *